United States Patent [19]

Hefner, Jr.

[11] Patent Number: 4,613,703

[45] Date of Patent: Sep. 23, 1986

[54] PROCESS FOR ALLYLATING HYDROXYAROMATIC COMPOUNDS

[75] Inventor: Robert E. Hefner, Jr., Lake Jackson, Tex.

[73] Assignee: The Dow Chemical Company, Midland, Mich.

[21] Appl. No.: 365,137

[22] Filed: Apr. 5, 1982

[51] Int. Cl.$^4$ ............................................. C07C 41/16
[52] U.S. Cl. ..................................... 568/640; 568/23; 568/33; 568/27; 568/48; 568/49; 568/53; 568/315; 568/636; 568/638; 568/643; 568/657
[58] Field of Search .................. 568/657, 23, 643, 33, 568/27, 640, 53, 48, 49, 315, 638, 636

[56] References Cited

U.S. PATENT DOCUMENTS

| | | | |
|---|---|---|---|
| 2,560,350 | 7/1951 | Jelinek | 167/30 |
| 2,968,679 | 1/1961 | Aelony | 260/612 |
| 3,060,243 | 10/1962 | Ham | 260/613 |
| 3,198,842 | 8/1965 | Berrigan | 260/624 |
| 4,229,356 | 10/1980 | Tabushi et al. | 260/396 K |

FOREIGN PATENT DOCUMENTS

| | | | |
|---|---|---|---|
| 923774 | 4/1963 | United Kingdom . | |
| 2035322 | 6/1980 | United Kingdom | 568/657 |

OTHER PUBLICATIONS

Tarbell, *Organic Reactions*, vol. II (1944), 1-3, 22-29.
March, J., *Advanced Organic Chemistry*, 1968, pp. 830-834.
Starks, C. M., *Journal of the American Chemical Society*, 1971, vol. 93, No. 1, pp. 195-198.

*Primary Examiner*—Bernard Helfin
*Attorney, Agent, or Firm*—Paul D. Hayhurst

[57] ABSTRACT

An isomeric mixture of C- and O-allylated aromatic compounds is prepared by contacting an allyl halide, a hydroxyaromatic reactant, an alkaline agent, water and a quaternary salt catalyst. This mixture may be thermally isomerized to obtain the C-allylated compounds in high yield.

20 Claims, No Drawings

PROCESS FOR ALLYLATING HYDROXYAROMATIC COMPOUNDS

BACKGROUND OF THE INVENTION

This invention relates to the catalytic allylation of hydroxyaromatic reactants. More specifically, it relates to a catalytic process for allylating hydroxyaromatic reactants in a system which is generally free of organic solvents.

U.S. Pat. No. 2,560,350 discloses the preparation of 2,2-bis(para-allyloxyphenyl)propane by reaction of an allyl halide, such as allyl chloride or allyl bromide, with 4,4'-isopropylidenediphenol, in an essentially anhydrous medium of ethanol or acetone in the presence of an HCl or HBr acceptor such as anhydrous potassium carbonate. A reaction time, at reflux temperature, of about 9 hours was reported to be necessary to complete the reaction and the product yield reported by this method was only about 49 percent. Furthermore, treatment of the resultant product mixture with an aqueous caustic solution was required to remove unreacted 4,4'-isopropylidenediphenol. This latter treatment resulted in the formation of salts which were insoluble in the reaction mixture. The formation of the salts produced an undesirable solid-liquid mixture from which the product had to be recovered and purified.

More recently, U.S. Pat. No. 3,060,243 disclosed the preparation of 2,2-bis(para-allyloxyphenyl)propane by reaction of an allyl halide with 4,4'-isopropylidenediphenol and an alkali metal hydroxide in a reaction solvent system composed of a binary mixture of water and an inert water-soluble organic solvent such as ethanol, tetrahydrofuran, acetonitrile, acetone, p-dioxane and the like. Alternatively, the patent discloses a method whereby the 4,4'-isopropylidenediphenol and the alkali metal hydroxide can be dissolved separately in the organic solvent and the water, respectively, followed by mixing the two solutions and adding the allyl halide.

It would be highly desirable to provide a method for allylating hydroxyaromatic compounds which would not require an organic solvent and which would produce the desired compounds in higher yields and at higher conversions than the methods previously described.

SUMMARY OF THE INVENTION

The present invention is such a method for allylating hydroxyaromatic compounds by contacting an allyl halide with a hydroxyaromatic compound in the presence of a catalyst and under conditions sufficient to form a composition which includes the corresponding C-allylated and, optionally, O-allylated aromatic compounds. Surprisingly, the practice of the process of this invention does not require an organic solvent and uses water as a portion of the reaction medium. More importantly, the practice of said process provides the user with a means of obtaining C-diallylated hydroxyaromatic compounds in yields and conversions higher than those obtainable by the methods of the prior art.

The products of the aforementioned process may be thermally rearranged to provide only the corresponding C-allylated compounds in high conversion and yield, based on the hydroxyaromatic starting materials. The C-allylated compounds produced are useful, among other things, as precursors to a number of known polymers. See, e.g., British Pat. No. 923,774.

DETAILED DESCRIPTION OF THE INVENTION

Hydroxyaromatic compounds are suitably employed in the practice of this invention and are aromatic or alkylaromatic compounds which bear one or more hydroxyl moieties. These compounds are generally represented by formula II,

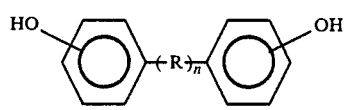

wherein R is independently —O—, —S—, —S—S—,

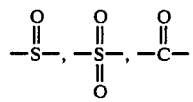

or a divalent hydrocarbon group having from 1 to about 8, preferably 1 to about 4, carbon atoms, and wherein n is zero or one. Preferred hydroxyaromatic reactants are those aromatic compounds wherein the two hydroxyl moieties are in the 4 and 4' positions and further wherein n is 1, with the proviso that if R is a divalent hydrocarbon radical, it will have from 1 to about 4 carbon atoms. The most preferred hydroxyaromatic reactant is 4,4'-isopropylidenediphenol. The hydroxyaromatic reactants may bear groups or substituents which do not interfere with the allylation reaction of this invention or the subsequent thermal rearrangement.

Allyl halides suitably employed in the practice of this invention are represented by formula I, $$H_2C=CH-CH_2X \qquad I$$

wherein X is Cl, Br or I. Preferred allyl halides are allyl chloride and allyl bromide. The most preferred allyl halide is allyl chloride. The allyl halide is usually employed in an amount which will provide a mixture of diallylated products such that very little or, preferably, no mono-allylated compounds will be in the mixture of diallylated products. Typically, an allyl halide aromatic hydroxyl group molar ratio of from about 1:1 to about 5:1, respectively, is employed. Preferably, this ratio will be from about 1:1 to about 2:1. It should be noted that an excess of allyl halide may be necessary to achieve the desired results when the reaction vessel is one which allows some of the allyl halide to escape the reaction mixture never to return thereto.

An alkaline agent is employed in the practice of the present invention for the purpose of increasing conversion to the diallylated product. For example, the alkaline agent may be an alkali metal hydroxide or an alkaline earth metal hydroxide. Preferred alkaline agents are KOH, NaOH or mixtures thereof. Sodium hydroxide is the most preferred alkaline agent. The alkaline agent is typically employed in order to provide a ratio of from about 1 to about 2 moles of alkali metal hydroxide per mole of hydroxy moieties originally present on the hydroxyaromatic reactant. Preferably this ratio will be from about 1 to about 1.25.

Water is typically employed in the process of this invention for the purpose of solubilizing transient phenate salts and coproduced alkali or alkaline earth metal salts. Further, water facilitates resolution of the diallylated products from water-soluble catalysts, coproduced salts, and residual alkaline agent, if any. Generally, from about 1 to about 20 moles of water will be employed per mole of hydroxyaromatic reactant. Using more than this amount of water is disadvantageous because of dilution of the alkaline agent, catalyst and allyl halide. In addition, the use of excess water requires more energy in order to maintain a given elevated reaction temperature. Using less water than the previously indicated minimum is disadvantageous because it may result in inadequate mixing and dissolution of the reactants, as well as inadequate separation of the diallylated product.

A catalyst is advantageously employed in the process of the present invention for the purpose of providing higher yields of diallylated products and higher conversion of the hydroxyaromatic reactants to the desired products. In many cases the catalyst speeds the rate of reaction and improves and speeds the dissolution of transient phenate salts. Suitable catalysts are quaternary salts and are represented by formula III,

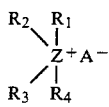

wherein Z is a tetravalent ammonium or phosphonium ion, A is any suitable counterion, and each $R_1$, $R_2$, $R_3$ and $R_4$ is independently an alkyl, aromatic or alkylaromatic moiety containing from 1 to about 18 carbon atoms.

Tetravalent ammonium ions are the preferred Z cations in formula III. Typical A counterions include chloride, bromide, iodide and hydroxyl ions. Chloride is the preferred A counterion. Quaternary ammonium halides are preferred catalysts. Tetraalkyl ammonium halides where the sum of the number of carbon atoms in the alkyl groups $R_1$, $R_2$, $R_3$ and $R_4$ is 16 or less, and benzyltrialkyl ammonium halides, such as benzyltrimethyl ammonium halides, are the most preferred catalysts. Any amount of catalyst may be employed as long as that amount is sufficient to catalyze the reaction. Typically, from about 0.0001 to about 0.1 mole of catalyst is employed per mole of hydroxy-aromatic reactant. Preferably, from about 0.001 to about 0.05 mole of catalyst is employed per mole of hydroxyaromatic reactant.

Catalytic quaternary salts may be bound in a polymeric support in the form of ion-exchange resins. Typical ion-exchange resins are those which bear quaternary ammonium salts on macroporous styrene-divinylbenzene resins. Examples of these bound quaternary salts include DOWEX ® MSA-1 and the like. The ion-exchange resin form of catalyst is advantageous in that it is easily recovered or, if used in a fixed bed, obviates the need for a catalyst recovery step. It should be noted that a catalyst bound in a polymeric support does not go into solution when used in accordance with the method of the present invention. Preferably, when solid particles of bound catalyst are employed, they will be uniformly dispersed in the reaction mixture or will form a fixed bed.

The reactants may be combined in any order. However, it is preferred to add the hydroxyaromatic reactant to a mixture of water, alkaline agent, and catalyst, and to add the allyl halide as the last component. It is equally preferred to add the hydroxyaromatic reactant and the catalyst first, followed by the alkaline agent and water, then followed by the allyl halide.

The reaction is typically conducted at a temperature of from about 25° C. to about 100° C. at atmospheric pressure. At temperatures below 25° C. the reaction proceeds more slowly. Temperatures greater than 100° C. may be employed but may lead to catalyst instability, which is undesirable. If a temperature higher than 100° C. is employed, pressures higher than atmospheric pressure should then be employed to reduce the loss of water and allyl halide. A temperature of from about 50° C. to about 80° C. is preferred.

The reaction time is a function of temperature, type and concentration of catalyst and the concentration of the hydroxyaromatic reactant. The reaction to form the isomeric mixture typically takes between about 2 and about 12 hours, not including the time needed for thermal rearrangement.

When the reactants, alkaline agent, catalyst and water are properly combined under reaction conditions as hereinbefore specified, a product mixture will be formed. At least one component of the isomeric product mixture will be allylated and will correspond structurally to the particular hydroxyaromatic reactant used as a starting material. The products formed are generally represented by the formula

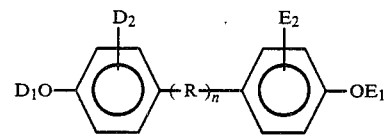

wherein one member of each of the following two pairs ($D_1$ and $D_2$) and ($E_1$ and $E_2$) is —H and the other is —$CH_2$—CH=$CH_2$, and wherein R and n are as previously defined. Typically, the product will be a mixture of C-allylated and O-allylated isomers, with $E_2$ and $D_2$ being attached to the carbons adjacent to the 4 and 4' positions. Minor amounts of allylated isomers exist wherein both members of one of the following two pairs, ($D_1$ and $D_2$) or ($E_1$ and $E_2$), are —$CH_2$—CH=$CH_2$, the members of the other pair being —H. Other minor isomers are present wherein both members of either the pair ($D_1$ and $D_2$) or ($E_1$ and $E_2$) are —$CH_2$—CH=$CH_2$ and 1 member of the other pair is —$CH_2$—CH=$CH_2$, the other member being —H. Another minor group of isomers exists wherein both members of either the pair ($D_1$ and $D_2$) or ($E_1$ and $E_2$) are —H and 1 member of the other pair is —H, the other member being —$CH_2$—CH=$CH_2$.

The mixture of isomers may be rearranged thermally using well-known techniques to convert the O-allylated isomers into C-allylated isomers. See, e.g., J. March, *Advanced Organic Chemistry*, pp. 830–834 (1968). For example, when 4,4'-isopropylidenediphenol is the hydroxyaromatic reactant, the isomeric mixture produced by the process of the present invention may be subjected to thermally induced isomerization to give 2,2'-bis(3-allylphenyl-4-hydroxy)propane in high conversion and yield. The thermal isomerization may be carried out before or after removal of the catalyst used in the process of this invention.

SPECIFIC EMBODIMENTS AND COMPARATIVE EXPERIMENTS

The following examples and comparative experiments are given to illustrate the invention and should not be construed as limiting its scope.

I. General Procedure

In a 500-ml, 3-necked round-bottom glass flask equipped with a thermostatically controlled heating means, a thermometer, a magnetic stirring apparatus, a condenser and a side-arm, vented addition funnel, a series of reactions are conducted. One-tenth of a mole of 4,4'-isopropylidenediphenol is added to the flask then 0.01 mole of a catalyst is added. The flask is blanketed with nitrogen gas to purge the flask of atmospheric air. The nitrogen blanket is maintained during the reaction. An aqueous sodium hydroxide solution, composed of 0.21 mole of NaOH and 150.0 g of deionized water, is then added to the flask, stirring is started, and a slurry forms. The contents of the flask are heated to a temperature of 50° C.–52° C. The slurry transforms into a solution except when certain catalysts, e.g., tetrabutyl ammonium bromide and tetraphenyl phosphonium chloride, are employed, in which cases the slurry remains throughout the heating stage.

At this point, 0.30 mole of allyl chloride is added, dropwise, over a period of 1 hour, to the mixture in the flask. A hazy solution forms after the first aliquot of allyl chloride is added. The addition of the remaining allyl chloride produces a cloudy slurry of oil in the aqueous phase.

After a 7-hour period during which the reaction temperature is maintained, each product slurry is held at approximately room temperature (25° C.) and is adjusted to pH 3.0 with aqueous hydrochloric acid. The resulting organic and aqueous layers are resolved in a separatory funnel and the nonaqueous layer is removed and weighed. Optionally, a small amount of toluene is used to speed the resolution of the organic and aqueous layers. The organic oil product optionally is dried over anhydrous sodium sulfate, then filtered or dried under reduce pressure using toluene as an azeotroping agent, and weighed. Nuclear magnetic resonance spectroscopic analysis is used to assess the percentage of diallylation and the percentage of O- and C-allylated functionalities present in the product.

II. Results

The results of several examples and comparative experiments are given in the following table. The results clearly indicate that higher yields and higher mole percentages of diallylated product are obtained using the method of the present invention than are obtained using the non-catalytic method of the comparative experiments. The aforementioned General Procedure is used except where specific exceptions are noted. Percent diallylation refers to the number of moles of diallylated product divided by the number of moles of dihydroxyaromatic starting material originally present. For example, 100 percent diallylation means that the product has one allyl group for every hydroxyl group which was on the hydroxyaromatic reactant.

TABLE I

Catalytic Diallylation of 4,4'-Isopropylidenediphenol

| Example | Catalyst | % Diallylation | % C-Allyl Functionality | Isolated Product (g) | Isolated Yield (mole %) |
|---------|----------|----------------|-------------------------|----------------------|-------------------------|
| 1 | tetramethyl ammonium chloride | 99.0 | 17.9 | 30.2 | 98.1 |
| 2 | tetramethyl ammonium bromide | 98.4 | 20.6 | 29.9 | 97.1 |
| 3 | tetrabutyl ammonium bromide | 99.9 | 25.2 | 31.8* | not calculated |
| 4** | tetramethyl ammonium chloride | 100.0 | 15.4 | 29.6 | 96.1 |
| 5 | DOWEX ® MSA-1 chloride form (5.0 grams wet resin) | 99.1 | 15.3 | 29.6 | 96.1 |
| 6** | benzyltrimethyl ammonium chloride | 100.0 | 15.4 | 29.6 | 96.1 |
| A*** | none | 89.5 | 16.7 | 26.8 | <88.7 |
| B**, *** | none | 91.4 | 20.4 | 27.5 | <90.0 |

*Isolated product is contaminated with catalyst.
**Performed at 60° C.–62° C.
***Not an embodiment of this invention; a comparative experiment.

EXAMPLE 7

Thermal isomerization of the product of Example 4 is carried out using the aforementioned equipment. The O- and C-diallylated product is charged to the reaction flask which is maintained under a continuous nitrogen blanket. The product mixture is stirred and heated until the desired reaction temperature of 200° C. is achieved. After 1.5 hours of reaction, the C-diallylated reaction product is cooled and weighed. Nuclear magnetic resonance spectroscopy is used to assess the percentage of C-allylated functionality in the product. Only the C-allylated product is observed, and it is recovered in 99.6 percent isolated yield.

What is claimed is:

1. A process which comprises contacting an allyl halide of formula I,

$$H_2C=CH-CH_2X$$

wherein X is Cl, Br or I, with a hydroxyaromatic compound of formula II,

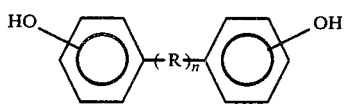

wherein R is independently —O—, —S—, —S—S—,

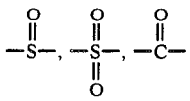

or a divalent hydrocarbon group having from 1 to about 8 carbon atoms, and wherein n is zero or one; in the substantial absence of an organic solvent and in the presence of an alkaline agent and a catalytic amount of a quaternary salt represented by formula III

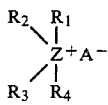

wherein Z is a tetravalent ammonium or phosphonium ion, A is any suitable counterion, and each $R_1$, $R_2$, $R_3$ and $R_4$ is independently an alkyl, aromatic or alkyl aromatic moiety containing from 1 to about 18 carbon atoms; and under reaction conditions sufficient to form a composition which includes the C-allylated and, optionally, O-allylated diallylated aromatic compounds which correspond structurally to be hydroxyaromatic compound of formula II.

2. The process of claim 1 wherein the allyl halide is allyl chloride or allyl bromide.

3. The process of claim 2 wherein the catalyst is a tetravalent ammonium ion and the A counterion is chloride.

4. The process of claim 3 wherein the hydroxyl moieties are in the 4 and 4' positions of the hydroxyaromatic reactant.

5. The process of claim 4 wherein the alkaline agent comprises KOH, NaOH and mixtures thereof.

6. The process of claim 5 wherein n is 1, with the proviso that if R is a divalent hydrocarbon, it will have from 1 to 4 carbon atoms.

7. The process of claim 6 wherein the total number of carbon atoms in the alkyl groups $R_1$, $R_2$, $R_3$ and $R_4$ is 16 or less.

8. The process of claim 7 wherein the allyl halide is allyl chloride.

9. The process of claim 8 wherein the catalyst is selected from the group consisting of:
(a) those wherein any one of the groups $R_1$, $R_2$, $R_3$ an $R_4$ is benzyl and the other three of said groups are methyl;
(b) tetraalkyl ammonium chlorides wherein each alkyl is identical and has from 1 to about 3 carbon atoms; and
(c) quaternary ammonium salts which are bound in a polymeric support.

10. The process of claim 9 wherein the alkaline agent is NaOH.

11. The process of claim 10 wherein the hydroxyaromatic reactant is 4,4'-isopropylidenediphenol.

12. The process of claim 11 wherein the hydroxyaromatic reactant is 4,4'-isopropylidenediphenol and the allyl halide is allyl chloride, and wherein these two compounds are contacted in the presence of water and sodium hydroxide such that a mixture of C-allylated and O-allylated aromatic compounds are formed which correspond to the structure of diallylated 4,4'-isopropylidenediphenol.

13. The process of claim 12 wherein the temperature is from about 25° C. to about 100° C.

14. A process comprising contacting an allyl halide with a hydroxyaromatic compound in the presence of a catalyst, water and an alkaline agent, and under reaction conditions sufficient to form a composition which includes a mixture of C- and O-allylated aromatic isomers, with the proviso that the yield of diallylated isomeric products is greater than 90.9 mole percent.

15. The process of claim 1 wherein the percent diallylation is greater than 91.4 mole percent.

16. The process of claim 1 wherein the yield is greater than 90.9 mole percent.

17. The process of claim 14 wherein the percent diallylation is greater than 91.4 mole percent.

18. The process of claim 14 wherein a catalytic quaternary salt is bound in a polymeric support.

19. The process of claim 14 wherein the alkaline agent comprises an alkali metal hydroxide or an alkaline earth metal hydroxide.

20. The process of claim 14 wherein the temperature is from about 50° C. to about 80° C.

* * * * *

UNITED STATES PATENT AND TRADEMARK OFFICE
CERTIFICATE OF CORRECTION

PATENT NO. : 4,613,703
DATED : Sept. 23, 1986
INVENTOR(S) : Robert E. Hefner, Jr.

It is certified that error appears in the above-identified patent and that said Letters Patent is hereby corrected as shown below:

Col. 5, line 66, delete "reduce" and insert --reduced--.

Col. 6, Table I, last column, Example B, delete "<90.0" and insert --<90.9--.

Col. 7, line 34, delete "be" and insert --the--.

Signed and Sealed this

Thirty-first Day of March, 1987

*Attest:*

DONALD J. QUIGG

*Attesting Officer*     *Commissioner of Patents and Trademarks*